(12) United States Patent
Ono (10) Patent No.: US 8,674,107 B2
(45) Date of Patent: Mar. 18, 2014

(54) CRYSTAL OF ANTI-BACTERIAL COMPOUND

(75) Inventor: Makoto Ono, Tokyo (JP)

(73) Assignee: Daiichi Sankyo Company, Limited, Tokyo (JP)

( * ) Notice: Subject to any disclaimer, the term of this patent is extended or adjusted under 35 U.S.C. 154(b) by 0 days.

(21) Appl. No.: 13/814,534

(22) PCT Filed: Aug. 5, 2011

(86) PCT No.: PCT/JP2011/067928

§ 371 (c)(1),
(2), (4) Date: Feb. 6, 2013

(87) PCT Pub. No.: WO2012/018105

PCT Pub. Date: Feb. 9, 2012

(65) Prior Publication Data

US 2013/0137723 A1 May 30, 2013
US 2013/0338189 A9 Dec. 19, 2013

(30) Foreign Application Priority Data

Aug. 6, 2010 (JP) ................................. 2010-177253

(51) Int. Cl.
*C07D 215/38* (2006.01)
*A61K 31/04* (2006.01)

(52) U.S. Cl.
USPC .......................................... 546/156; 514/312

(58) Field of Classification Search
USPC .......................................... 546/156; 514/312
See application file for complete search history.

(56) References Cited

U.S. PATENT DOCUMENTS

| 6,900,225 B2 * | 5/2005 | Takemura et al. ............ 514/312 |
| 2003/0187008 A1 | 10/2003 | Takemura et al. |
| 2012/0108582 A1 * | 5/2012 | Takahashi et al. ......... 514/230.2 |
| 2013/0029977 A9 | 1/2013 | Takahashi et al. |

FOREIGN PATENT DOCUMENTS

| WO | 01/72738 A1 | 10/2001 |
| WO | 03/076428 A1 | 9/2003 |
| WO | 2008/082009 A2 | 7/2008 |

* cited by examiner

*Primary Examiner* — D M Seaman
(74) *Attorney, Agent, or Firm* — Dorsey and Whitney LLP (57) ABSTRACT

It is intended to provide a salt of a compound and crystals thereof useful as a therapeutic and/or preventive agent for infectious diseases which has wide and excellent antibacterial activity and has excellent safety.
[Solution]
The present invention provides the hydrochloride of 7-[(1R, 5S)-1 -amino-5-fluoro-3-azabicyclo[3.3.0]octan-3-yl]-6-fluoro-1-[(1R,2S)-2 -fluorocyclopropan-1-yl]-1,4-dihydro-8-methyl-4-oxoquinoline-3-carboxylic acid and crystals thereof, as a novel salt form of the compound and crystals thereof.

12 Claims, 10 Drawing Sheets

CRYSTAL OF ANTI-BACTERIAL COMPOUND

This application is a national stage application under 35 U.S.C. §371 of International Application No. PCT/JP2011/067928, filed Aug. 5, 2011, entitled "Crystal of Antibacterial Compound," which claims priority to Japanese Patent Application No. 2010-177253, filed Aug. 6, 2010, the contents of all of which are hereby incorporated in their entirety by reference.

TECHNICAL FIELD

The present invention relates to a salt of a compound and a crystal thereof useful as a therapeutic and/or preventive agent for infectious diseases which has excellent antibacterial activity against a wide range of bacteria, including resistant bacteria, and also has excellent safety.

BACKGROUND ART

A compound represented by the following structural formula:

[Formula 1]

that is, 7-[(1R,5S)-1-amino-5-fluoro-3-azabicyclo[3.3.0]octan-3-yl]-6-fluoro-1-[(1R,2S)-2-fluorocyclopropan-1-yl]-1,4-dihydro-8-methyl-4-oxoquinoline-3-carboxylic acid (hereinafter, referred to as compound A), has wide and strong antibacterial activity against Gram-positive bacteria, notably against resistant Gram-positive cocci such as multiple resistant pneumococcus including quinolone resistant, and against Gram-negative bacteria. Compound A also has such excellent safety that it causes only with low probability previously known side effects of antibacterial agents of this class such as convulsion induction and phototoxicity (photosensitivity) and recently clinically reported side effects such as cardiotoxicity (QT prolongation), blood glucose level abnormality, and delayed rash. It has also become clear that compound A shows excellent oral absorbability and permeability into organs. Thus, compound A is expected to be an excellent antibacterial agent (Patent Literature 1).

CITATION LIST

Patent Literature

Patent Literature 1: International Publication No. WO 2008/082009

SUMMARY OF INVENTION

Technical Problem

There has been a demand for the development of a novel form of compound A that is preferable as an active pharmaceutical ingredient.

Solution to Problem

The present inventor has conducted studies on acid-adduct salts such as various organic acid salts and inorganic acid salts to search for novel forms of compound A. Consequently, the present inventor has found that the hydrochloride, hydrobromide, sulfate, p-toluenesulfonate, or the like of this compound is excellent as an active pharmaceutical ingredient. The inventor has further confirmed that the monohydrochloride dihydrate of compound A, having excellent properties in terms of moisture absorption and desorption properties, solubility, crystal stability, and chemical stability, is optimal as an active pharmaceutical ingredient thereof. These findings have led to the completion of the present invention.

Specifically, the present invention relates to:

[1] 7-[(1R,5S)-1-Amino-5-fluoro-3-azabicyclo[3.3.0]octan-3-yl]-6-fluoro-1-[(1R,2S)-2-fluorocyclopropan-1-yl]-1,4-dihydro-8-methyl-4-oxoquinoline-3-carboxylic acid monohydrochloride;

[2] 7-[(1R,5S)-1-amino-5-fluoro-3-azabicyclo[3.3.0]octan-3-yl]-6-fluoro-1-[(1R,2S)-2-fluorocyclopropan-1-yl]-1,4-dihydro-8-methyl-4-oxoquinoline-3-carboxylic acid monohydrochloride dihydrate;

[3] the compound according to [2], wherein the compound is a crystal;

[4] the compound according to [3], wherein the compound is a crystal having characteristic peaks at diffraction angles (2θ) of 5.3, 7.9, 10.6, 13.3, 21.1, 23.0, 25.1, and 27.6(°) in powder X-ray diffraction;

[5] a medicine comprising the compound according to any one of [1] to [4] as an active ingredient;

[6] a therapeutic agent for infections comprising the compound according to any one of [1] to [4] as an active ingredient;

[7] an antibacterial agent comprising the compound according to any one of [1] to [4] as an active ingredient; and

[8] a method for treating and/or preventing infections comprising administering the compound according to any one of [1] to [4].

In the present specification, "crystal" refers to a solid having three-dimensional regular repeats of constituting atoms (or populations thereof) forming its internal structure and is distinguished from amorphous solids, which do not have such an ordered internal structure.

In the present specification, "salt" also includes salts in solvate forms, for example, hydrate forms, unless otherwise specified.

In the present specification, "aqueous solvent" refers to a mixture of water and a solvent other than water. Examples thereof include a mixture of water and ethanol and a mixture of water and 2-propanol. A mixed solvent of water and ethanol is also referred to as aqueous ethanol, and a mixed solvent of water and 2-propanol is also referred to as aqueous 2-propanol.

In the present specification, "%" used in "% aqueous solvent" refers to the ratio of water in a mixed solvent of water and a solvent other than water. For example, aqueous ethanol having 20% of water is also referred to as 20% aqueous ethanol.

Compound A can be produced by a method described in Patent Literature 1 or a method equivalent thereto.

The acid-adduct salt as the salt of the present invention can be obtained, for example, by adding an equimolar amount of an acid to compound A and, if necessary, mixing or using an appropriate solvent or the like.

The crystal of the salt of the present invention can be produced, for example, by dissolving the hydrochloride of compound A in an appropriate solvent and supersaturating the salt by pH adjustment, solution concentration, temperature adjustment, or the like to precipitate crystals.

The precipitation of crystals may be started spontaneously in a reaction vessel and can also be started or promoted by inoculation of seed crystals, ultrasonic stimulation, or mechanical stimulation such as rubbing of the surface of the vessel.

The temperature for the crystallization of the salt of compound A is preferably 0° C. to 40° C., and more preferably 10° C. to 20° C.

The precipitated crystals can be isolated by, for example, filtration, centrifugation, or decantation. The isolated crystals can be washed, if necessary, with an appropriate solvent.

Examples of the solvent that can be used in the washing of the collected salt include water, ethanol, 2-propanol, acetone, ethyl acetate, toluene, acetonitrile, methyl acetate, and ether and preferably include ethanol and 2-propanol.

The purity and quality of the obtained crystals can be improved by recrystallization or slurry purification.

Recrystallization of the salt of the present invention can be achieved by a method usually used in the field of organic synthetic chemistry. Specific examples of the solvent that can be used in recrystallization of the acid-adduct salt of the compound of the present invention include water, methanol, ethanol, propanol, 2-propanol, acetone, aqueous methanol, aqueous ethanol, aqueous propanol, aqueous 2-propanol, aqueous acetone, and aqueous acetonitrile and preferably include aqueous methanol, aqueous ethanol, aqueous 2-propanol, aqueous acetone, and aqueous acetonitrile.

Slurry purification is the operation of suspending the crystals of the compound in an appropriate solvent, stirring the suspension, and then isolating crystals. Examples of the solvent that can be used in slurry purification of the salt crystals or the like of compound A of the present invention include water, methanol, ethanol, propanol, 2-propanol, acetonitrile, methylene chloride, toluene, methyl acetate, ethyl acetate, pentane, tetrahydrofuran, N,N-dimethylformamide, water, hexane, diisopropyl ether, ether, aqueous ethanol, aqueous propanol, aqueous 2-propanol, and aqueous acetone and preferably include water, methanol, ethanol, 2-propanol, acetone, acetonitrile, ethyl acetate, pentane, aqueous ethanol, aqueous 2-propanol, and aqueous acetone.

The isolated crystals can be dried usually at a temperature of 10° C. to 100° C., and preferably at a temperature of 30° C. to 50° C., until the weight substantially no longer changes. Drying of the crystals can be carried out, if necessary, in the presence of a drying agent such as silica gel or anhydrous calcium chloride and may be performed under reduced pressure.

The moisture content of the dried crystals may be controlled by moisture absorption usually at a temperature of 10° C. to 30° C. and a relative humidity of 20% to 90%, and preferably at a temperature of 20° C. to 30° C. and a relative humidity of 50% to 80%, until the weight substantially no longer changes.

Next, each acid-adduct salt of compound A will be described.

The hydrochloride of compound A is preferably the monohydrochloride and is present in the form of the monohydrate or the dihydrate. Either of these hydrates can be obtained depending on which hydrate is used as the raw material in recrystallization or slurry purification, the type and water content of the solvent used in this procedure, and the treatment temperature. The trend observed in the formation of these hydrates was that higher water contents worked in favor of the formation of the dihydrate while lower temperatures worked in favor of the formation of the dihydrate.

For example, in the treatment of the monohydrochloride dihydrate of compound A with aqueous 2-propanol, the dihydrate can be obtained at a treatment temperature of 5° C. or higher by using 2-propanol containing 7.5% or more of water as a solvent. Alternatively, the dihydrate can be obtained with 2.5% or more aqueous 2-propanol provided that the treatment temperature is set to 5° C.

By contrast, in the treatment of the monohydrochloride monohydrate of compound A, the monohydrate can be obtained at a treatment temperature of 35° C. or lower by using 2-propanol having a water content of 5% or less. However, even when the monohydrate is used, the dihydrate is obtained with 2-propanol having a water content of 10% or more. In the case of 2-propanol having a water content of 7.5%, the monohydrate can be obtained at a treatment temperature of 20° C. or higher whereas the dihydrate is obtained at a treatment temperature of 5° C.

The monohydrochloride dihydrate of compound A exhibited a solubility of 2 mg/mL or higher in each of water, the Japanese Pharmacopoeia (JP) 1st fluid for the dissolution test, the JP 2nd fluid for the dissolution test, fasted state simulated intestinal fluid (FaSSIF), and fed state simulated intestinal fluid (FeSSIF), demonstrating its excellent solubility.

During storage for 2 weeks under the respective conditions of a temperature of 60° C. and a humidity of 0% and a temperature of 40° C. and a humidity of 75%, related substances increased at rates as very low as 0.02% and 0.01%, respectively, also demonstrating excellent storage stability.

Figure 1:
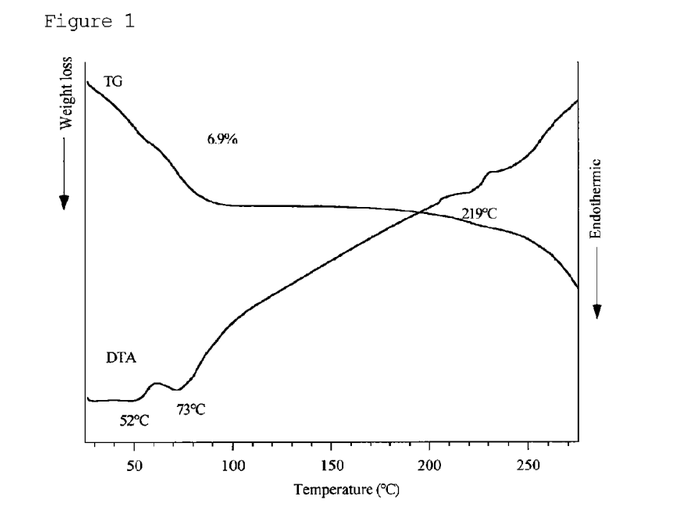
FIG. 1 is a diagram showing thermal analysis (TG/DTA) results of the monohydrochloride dihydrate of compound A.
Figure 2:
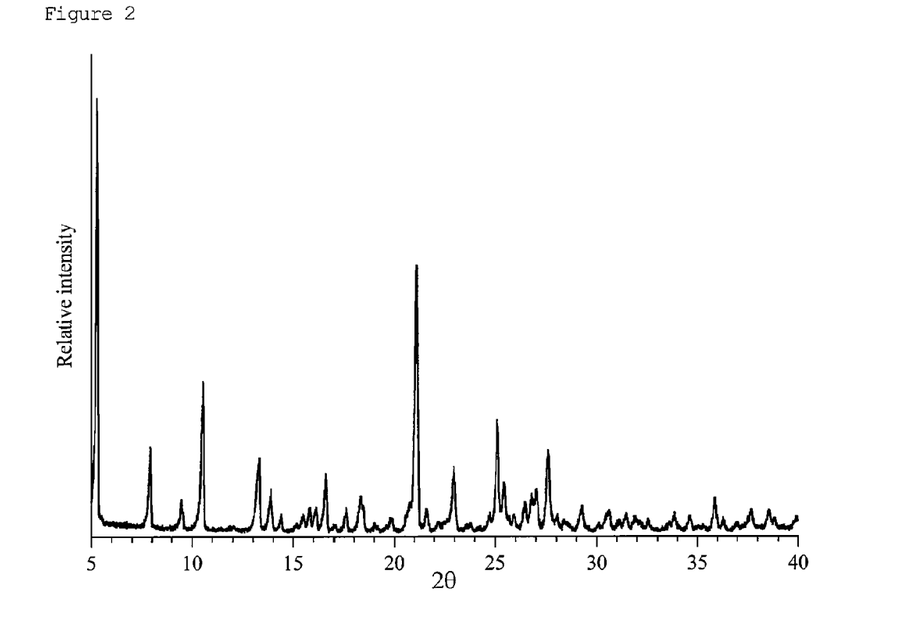
FIG. 2 is a diagram showing the powder X-ray diffraction of the monohydrochloride dihydrate of compound A.
Figure 3:
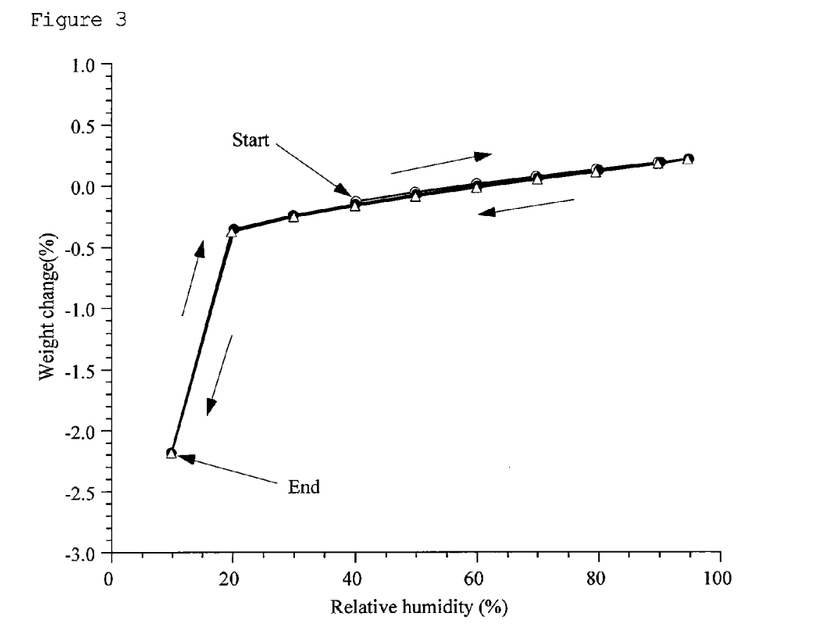
FIG. 3 is a diagram showing the moisture absorption and desorption properties of the monohydrochloride dihydrate of compound A.
Figure 4:
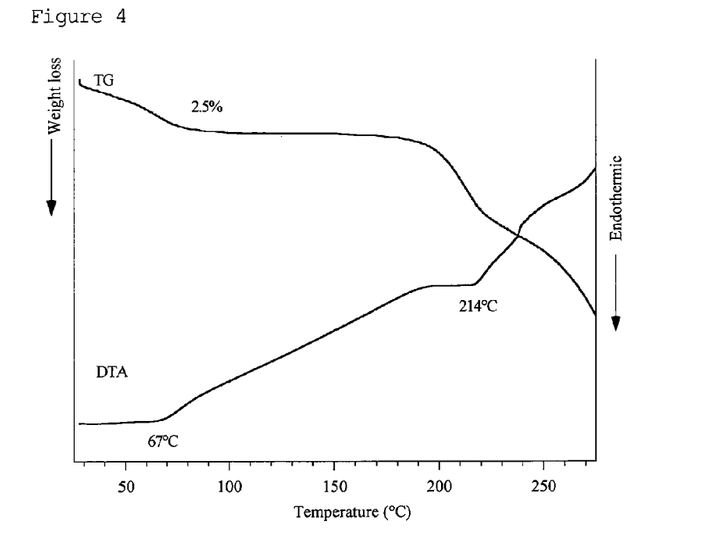
FIG. 4 is a diagram showing thermal analysis (TG/DTA) results of the monohydrochloride monohydrate of compound A.

As for moisture absorption and desorption properties, the change in weight was approximately 2% or less, and the absorption and desorption patterns were well consistent. In this regard, excellent properties were also confirmed (FIG. 3). The monohydrochloride dihydrate of compound A has characteristic peaks at diffraction angles (2θ) of 5.3, 7.9, 10.6, 13.3, 21.1, 23.0, 25.1, and 27.6(°) in powder X-ray diffraction (FIG. 2).

Figure 5:
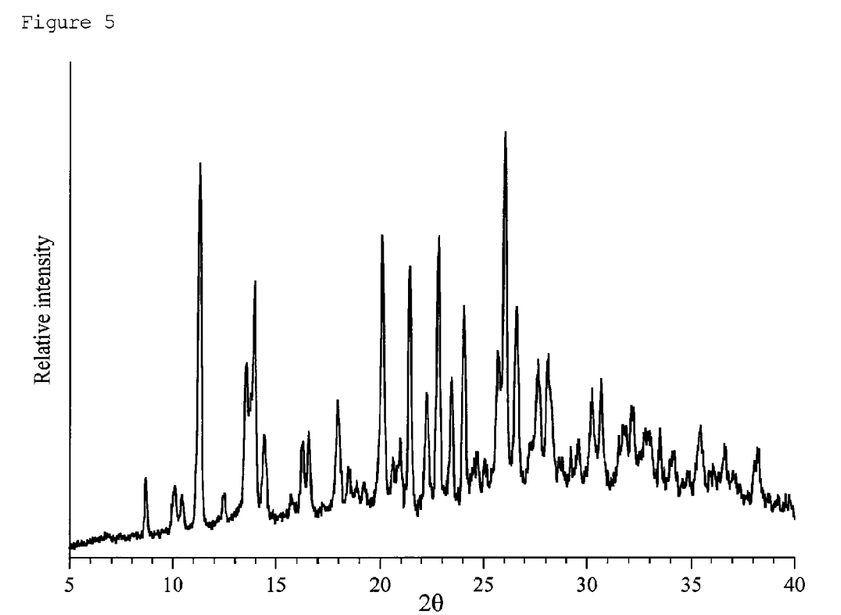
FIG. 5 is a diagram showing the powder X-ray diffraction of the monohydrochloride monohydrate of compound A.
Figure 6:
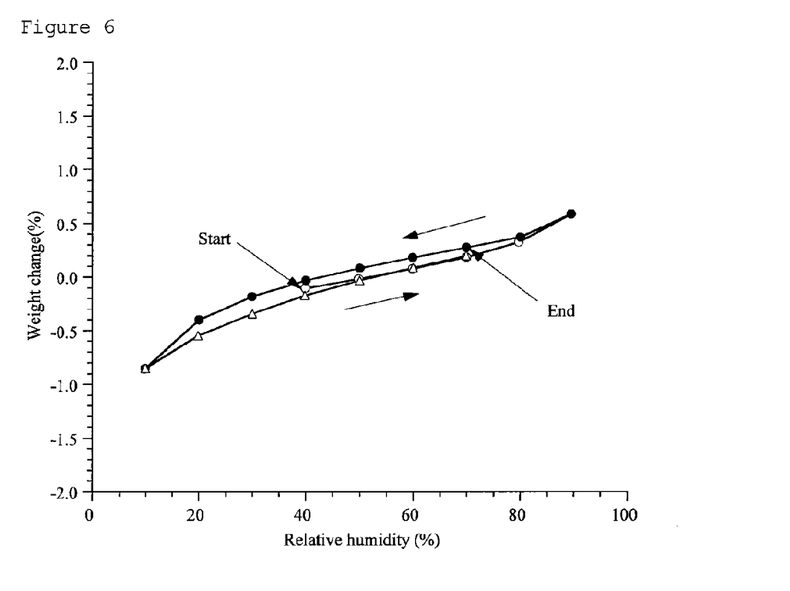
FIG. 6 is a diagram showing the moisture absorption and desorption properties of the monohydrochloride monohydrate of compound A.
Figure 7:
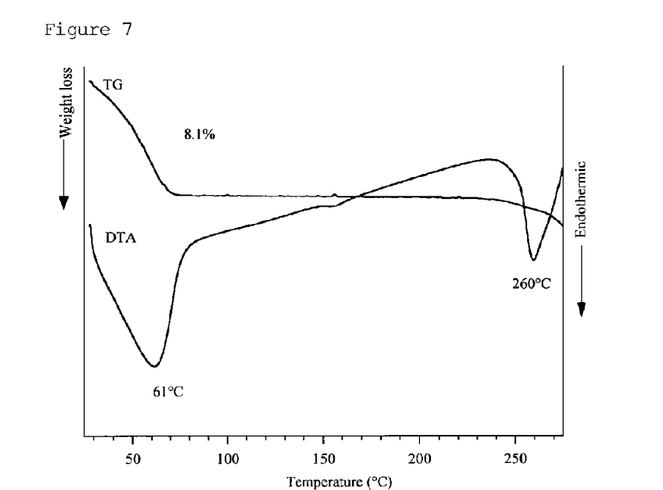
FIG. 7 is a diagram showing thermal analysis (TG/DTA) results of the hydrobromide-1 of compound A.

The monohydrochloride monohydrate of compound A can be obtained by preparation or purification in a solvent having a lower water content than that for the dihydrate. The change in weight of the monohydrochloride monohydrate was approximately 1% or less in terms of moisture absorption and desorption properties. In addition, the monohydrochloride monohydrate exhibited substantially the same moisture absorption and desorption patterns and was confirmed to have excellent properties (FIG. 6). The monohydrochloride monohydrate of compound A has characteristic peaks at diffraction angles (2θ) of 11.3, 14.0, 20.1, 21.4, 22.8, 24.0, 26.0, and 26.6(°) in powder X-ray diffraction (FIG. 5).

Figure 8:
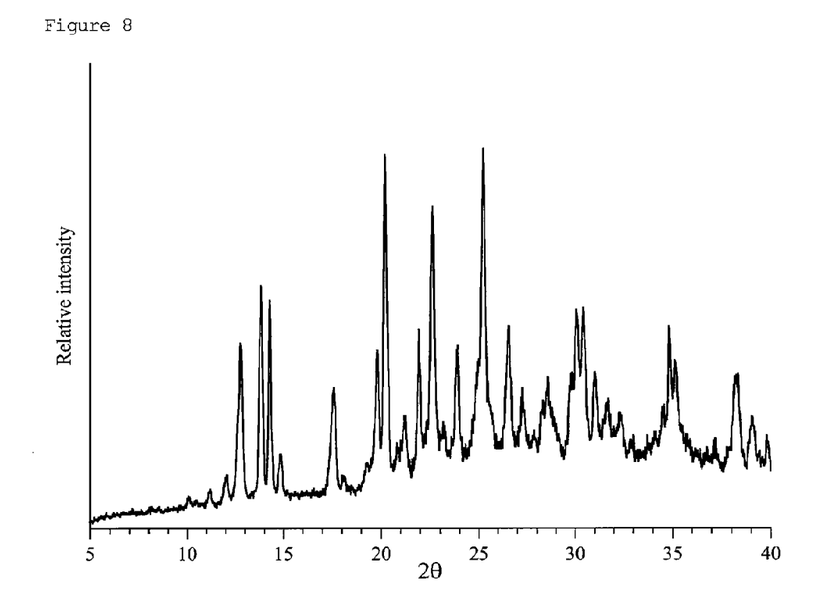
FIG. 8 is a diagram showing the powder X-ray diffraction of the hydrobromide-1 of compound A.
Figure 9:
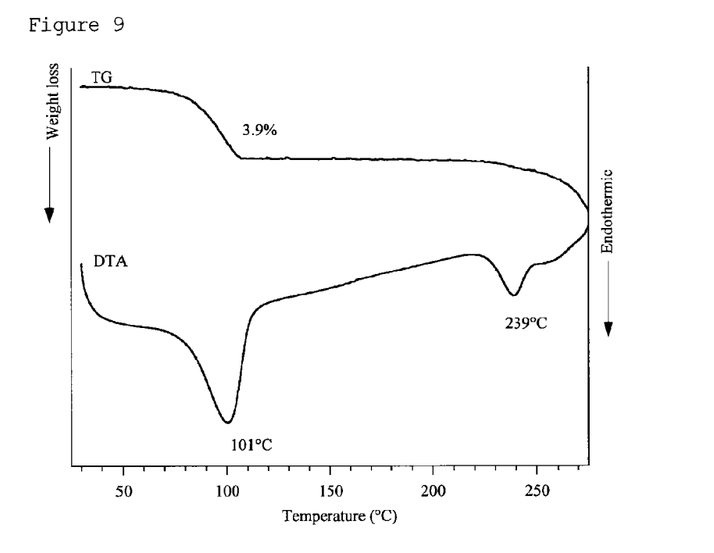
FIG. 9 is a diagram showing thermal analysis (TG/DTA) results of the hydrobromide-2 of compound A.
Figure 10:
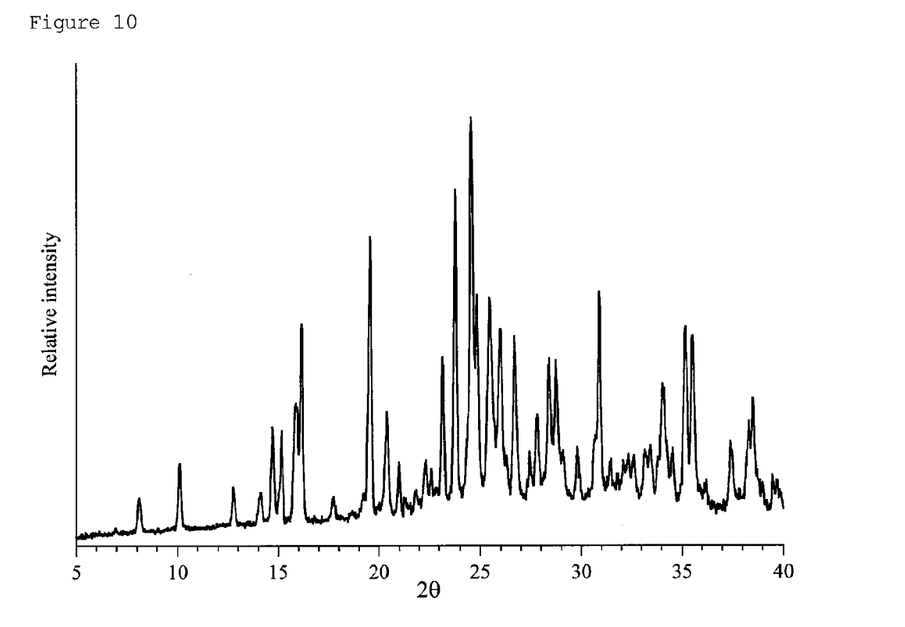
FIG. 10 is a diagram showing the powder X-ray diffraction of the hydrobromide-2 of compound A.
Figure 11:
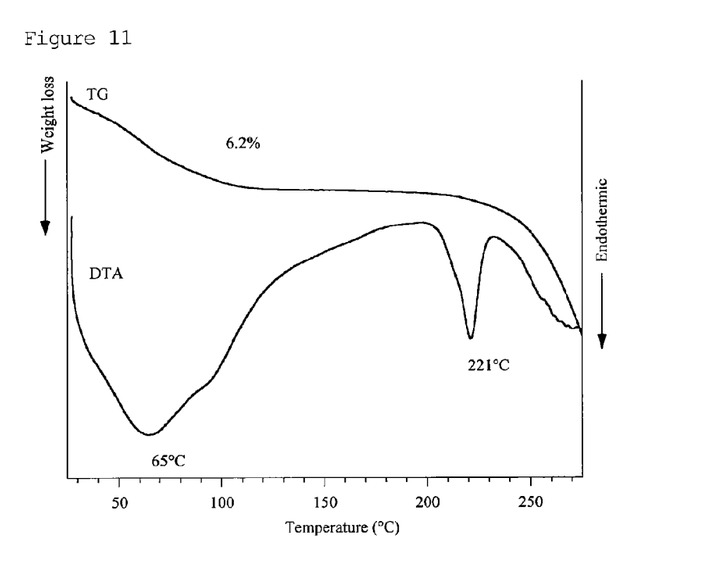
FIG. 11 is a diagram showing thermal analysis (TG/DTA) results of the sulfate of compound A.

The hydrobromide of compound A can be prepared similarly to its hydrochloride. The hydrobromide was found to include two types of crystal. The crystal of one of these two types has characteristic peaks at diffraction angles (2θ) of 13.8, 14.3, 20.2, 22.6, 25.2, 26.5, 30.0, and 31.0(°) in powder X-ray diffraction (FIG. 8). The crystal of the other type has characteristic peaks at diffraction angles (2θ) of 16.1, 19.5, 23.7, 24.6, 24.8, 25.5, 30.9, and 35.2(°) in powder X-ray diffraction (FIG. 10). From the results of thermal analysis, the former crystal is presumed to be a crystal of the dihydrate because of a change in weight as large as 8.1%, while the latter crystal is presumed to be a crystal of the monohydrate.

Figure 12:
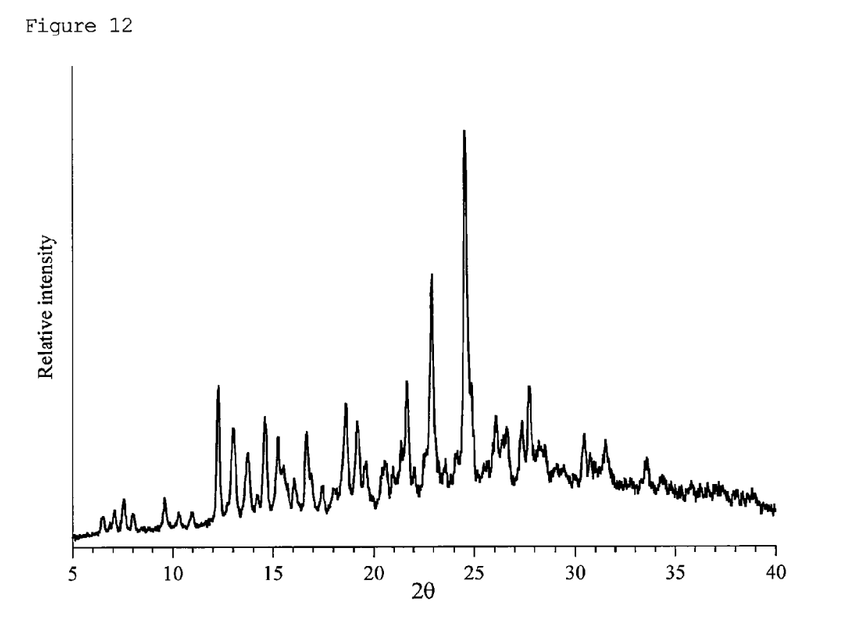
FIG. 12 is a diagram showing the powder X-ray diffraction of the sulfate of compound A.
Figure 13:
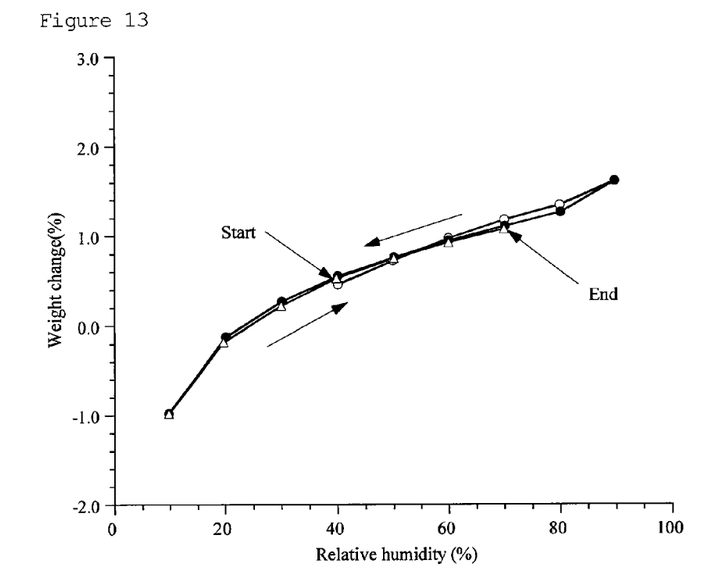
FIG. 13 is a diagram showing the moisture absorption and desorption properties of the sulfate of compound A.
Figure 14:
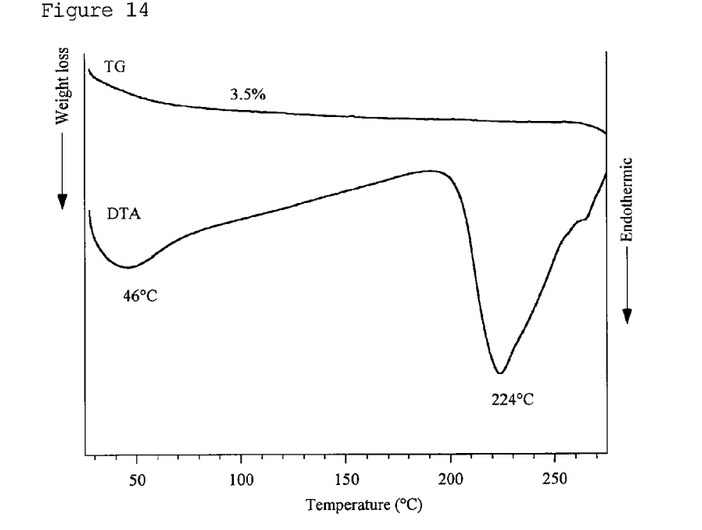
FIG. 14 is a diagram showing thermal analysis (TG/DTA) results of the p-toluenesulfonate of compound A.

The sulfate of compound A has excellent moisture absorption and desorption properties. Its moisture absorption and desorption patterns were well consistent. In addition, the change in weight was found to be approximately 2% or less (FIG. 13). The sulfate has characteristic peaks at diffraction angles (2θ) of 12.3, 14.6, 18.6, 21.7, 22.9, 24.6, 26.1, and 27.7(°) in powder X-ray diffraction (FIG. 12).

Figure 15:
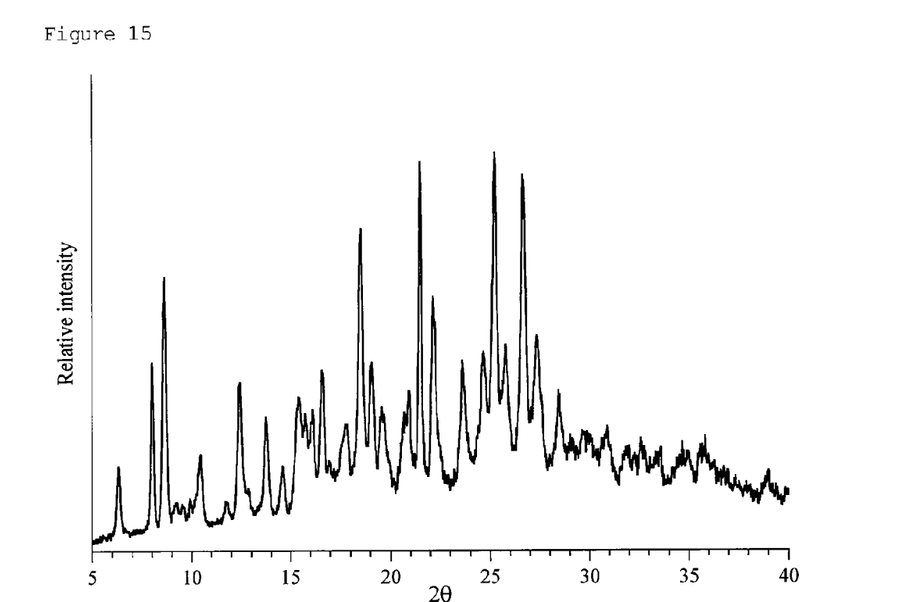
FIG. 15 is a diagram showing the powder X-ray diffraction of the p-toluenesulfonate of compound A.
Figure 16:
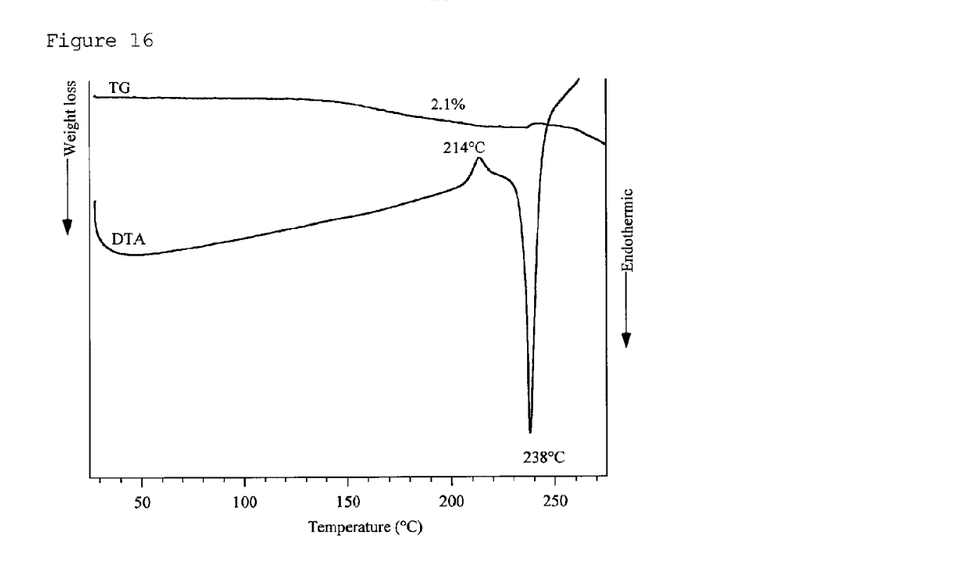
FIG. 16 is a diagram showing thermal analysis (TG/DTA) results of the free form-1 of compound A.

The p-toluenesulfonate of compound A has characteristic peaks at diffraction angles (2θ) of 8.0, 8.6, 18.5, 21.5, 22.2, 25.2, 25.8, and 27.4(°) in powder X-ray diffraction (FIG. 15).

Figure 17:
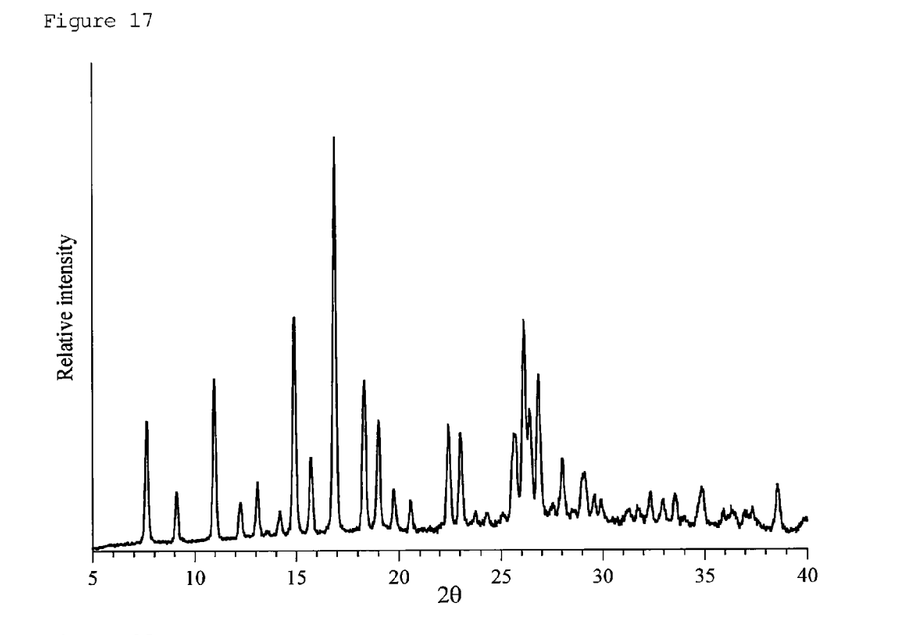
FIG. 17 is a diagram showing the powder X-ray diffraction of the free form-1 of compound A.
Figure 18:
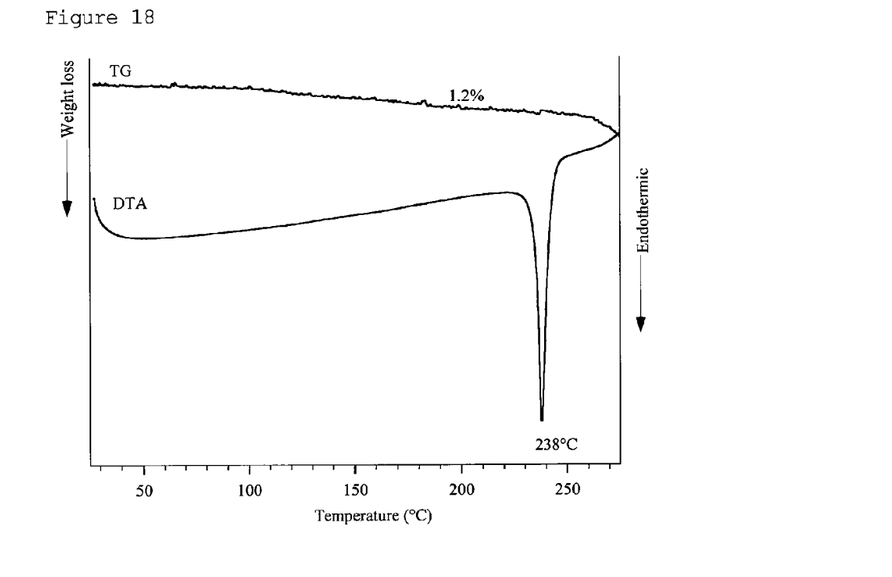
FIG. 18 is a diagram showing thermal analysis (TG/DTA) results of the free form-2 of compound A.
Figure 19:
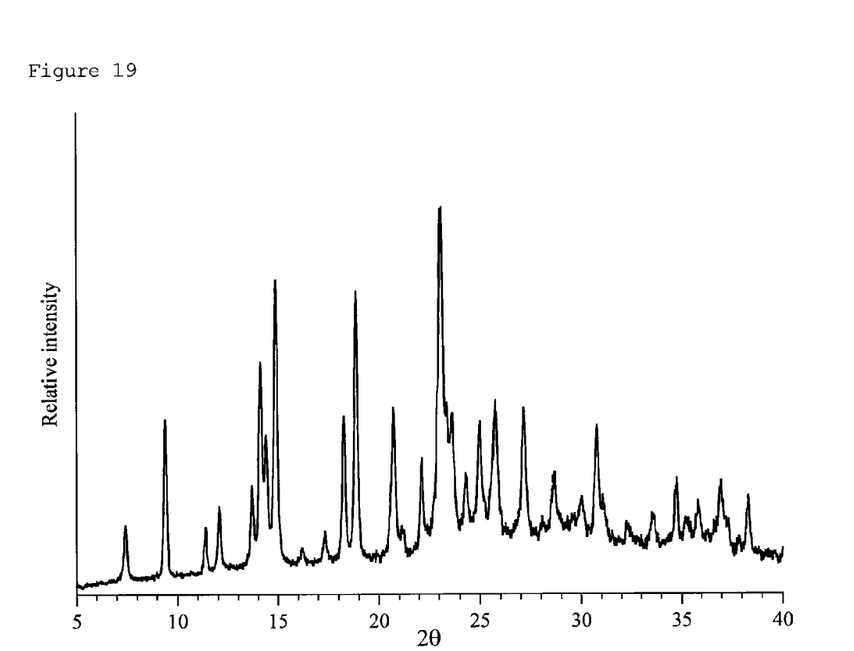
FIG. 19 is a diagram showing the powder X-ray diffraction of the free form-2 of compound A.

Compound A in the free form was found to include two types of crystal. The crystal of one of these two types has characteristic peaks at diffraction angles (2θ) of 7.6, 11.0, 14.9, 16.9, 18.3, 26.1, 26.4, and 26.9(°) in powder X-ray diffraction (FIG. 17). The crystal of the other type has characteristic peaks at diffraction angles (2θ) of 9.4, 14.1, 14.9, 18.9, 20.7, 23.1, 25.0, and 25.8(°) in powder X-ray diffraction (FIG. 19).

The salt and/or crystal of the present invention has strong antibacterial activity and therefore can be used as a medicine for humans, animals, and fish, an agricultural chemical, or a food preservative. The dose of the compound of the present invention used as a human medicine is 50 mg to 1 g, and more preferably 100 to 500 mg, per day for an adult. The dose for an animal varies depending on the purpose of administration, the size of the animal to be treated, the type of the pathogen with which the animal is infected, and the degree of the disease; the daily dose is generally 1 to 200 mg, and more preferably 5 to 100 mg, per kg body weight of the animal. The daily dose is administered once or in two to four divided doses. The daily dose may exceed the aforementioned dose if necessary.

The salt and/or crystal of the present invention is active against a wide range of microorganisms causing various infections and can treat, prevent, or relieve diseases caused by these pathogens. Examples of bacteria or bacteria-like microorganisms for which the compound of the present invention is effective include *Staphylococcus, Streptococcus pyogenes, hemolytic streptococcus, enterococcus, pneumococcus, Peptostreptococcus, gonococcus, Escherichia coli, Citrobacter, Shigella, Klebsiellapneumoniae, Enterobacter, Serratia, Proteus, Pseudomonas aeruginosa, Haemophilus influenzae, Acinetobacter, Campylobacter*, and *Chlamydia trachomatis*.

Examples of diseases caused by these pathogens include folliculitis, furuncle, carbuncle, erysipelas, cellulitis, lymphangitis (lymphadenitis), whitlow, subcutaneous abscess, hidradenitis, acne conglobata, infectious atheroma, perirectal abscess, mastitis, superficial secondary infection such as traumatic infection, burn infection, or surgical wound infection, laryngopharyngitis, acute bronchitis, tonsillitis, chronic bronchitis, bronchiectasis, diffuse panbronchiolitis, infection secondary to a chronic breathing disease, pneumonia, pyelonephritis, cystitis, prostatitis, epididymitis, gonococcal urethritis, nongonococcal urethritis, cholecystitis, cholangitis, shigellosis, enteritis, adnexitis, intrauterine infection, bartholinitis, blepharitis, hordeolum, dacryocystitis, meibomianitis, corneal ulcer, otitis media, sinusitis, periodontitis, pericoronitis, jaw inflammation, peritonitis, endocarditis, sepsis, meningitis, and skin infection.

Examples of *Mycobacterium* spp. for which the salt and/or crystal of the present invention is effective include tubercle bacilli (*Mycobacterium tuberculosis, M. bovis*, and *M. africanum*) and atypical mycobacteria (*M. kansasii, M. marinum, M. scrofulaceum, M. avium, M. intracellulare, M. xenopi, M. fortuitum*, and *M. chelonae*). Mycobacterial infections caused by these pathogens are broadly classified into three types: tuberculosis, atypical mycobacterial infections, and leprosy. *Mycobacterium tuberculosis* infections are observed in the thoracic cavity, trachea and bronchus, lymph node, systemic dissemination, bone joints, meninges and brain, digestive organs (intestine and liver), skin, mammary gland, eyes, middle ear and pharynx, urinary tract, male genital organs, and female genital organs, in addition to lung. Atypical mycobacterial infections (nontuberculous mycobacterial infections) mainly affect the lung, and may also appear as local lymphadenitis, soft skin tissue infection, osteoarthritis, or systemic dissemination-type infection.

The salt and/or crystal of the present invention is also effective for various microorganisms causing animal infections such as *Escherichia, Salmonella, Pasteurella, Haemophilus, Bordetella, Staphylococcus*, and *Mycoplasma*. Specific examples of animal diseases include bird diseases such as *Escherichia coli* disease, pullorum disease, fowl paratyphoid, fowl cholera, infectious coryza, staphylococcal disease, and mycoplasma infection; pig diseases such as *Escherichia coli* disease, salmonellosis, pasteurellosis, *hemophilus* infection, atrophic rhinitis, exudative epidermitis, and mycoplasma infection; bovine diseases such as *Escherichia coli* disease, *salmonellosis, hemorrhagic septicemia, mycoplasma* infection, contagious *bovine pleuropneumonia*, and *mastitis*; dog diseases such as *Escherichia coli* sepsis, *salmonella* infection, hemorrhagic septicemia, pyometra, and cystitis; and cat diseases such as exudative pleuritis, cystitis, chronic rhinitis, *hemophilus* infection, kitten diarrhea, and mycoplasma infection.

A medicine comprising the salt and/or crystal of the present invention as an active ingredient is preferably provided in the form of a pharmaceutical composition comprising the salt and/or crystal of the present invention as an active ingredient and one or two or more pharmaceutical additives. The dosage form of the medicine of the present invention is not particularly limited, and the medicine can be administered orally or parenterally.

The dosage form of an antibacterial agent containing the salt and/or crystal of the present invention can be appropriately selected according to the administration method and prepared by a method for preparing various preparations commonly used. Examples of the antibacterial agent dosage form containing the compound of the present invention as a main agent include tablets, powders, granules, capsules, solutions, syrups, elixirs, and oily or aqueous suspensions. An injection preparation may contain an additive such as a stabilizer, a preservative, or a solution adjuvant, and may be prepared before use from a solid preparation formed by storing a solution that may contain such an additive in a container and then lyophilizing the solution, for example. One dose may be stored in a container, or multiple doses may be stored in a single container. Examples of external preparations include solutions, suspensions, emulsions, ointments, gels, creams, lotions, and sprays. A solid preparation may contain a pharmaceutically acceptable additive together with the active compound. Examples of the additive include fillers, binders, disintegrants, solution promoters, wetting agents, and lubricants. A liquid preparation may be a solution, a suspension, an emulsion, or the like, and may contain an additive such as a suspending agent or an emulsifier.

Next, preparation examples will be described.

FORMULATION EXAMPLE 1

Capsules

| | |
|---|---|
| Monohydrochloride dihydrate of compound A | 100.0 mg |
| Corn starch | 23.0 mg |
| Calcium carboxymethylcellulose | 22.5 mg |
| Hydroxymethylcellulose | 3.0 mg |
| Magnesium stearate | 1.5 mg |
| Total | 150.0 mg |

FORMULATION EXAMPLE 2

Solution Preparation

| | | |
|---|---:|---|
| Monohydrochloride dihydrate of compound A | 1 to 10 | g |
| Acetic acid or sodium hydroxide | 0.5 to 2 | g |
| Ethyl p-oxybenzoate | 0.1 | g |
| Purified water | 87.9 to 98.4 | g |
| Total | 100 | g |

Advantageous Effects of Invention

The salt, particularly, the monohydrochloride dihydrate, of compound A of the present invention has favorable crystallinity and is excellent in moisture absorption and desorption properties, solubility, crystal stability, and chemical stability. Thus, the salt of compound A of the present invention is useful as an active pharmaceutical ingredient.

DESCRIPTION OF EMBODIMENTS

The present invention will be described below in detail with reference to examples; however, the present invention is not limited to the examples.

EXAMPLES

In the Examples below, powder X-ray diffraction, thermal analysis (TG/DTA), and elemental analysis were conducted under the following measurement conditions:

Measurement conditions for powder X-ray diffraction;

Radiation source: Cu-Kα rays, filter: Ni, detector: two-dimensional position-sensitive proportional counter, voltage of the counter: 40 kV, current of the counter: 40 mA, integration time: 120 seconds/frame, analysis range: 2θ=5–40°, apparatus: manufactured by Bruker Corp.

Measurement conditions for thermal analysis (TG/DTA);

Rate of temperature rise: 10° C./min., sample container: aluminum pan, reference substance: vacant aluminum pan, atmosphere: 200 mL/min. of nitrogen gas, sample volume: approximately 5 mg, apparatus: SSC5200 TG/DTA220 manufactured by SEIKO Instruments & Electronics Ltd.

Measurement conditions for elemental analysis;

Sample volume: approximately 2 mg, CHN analysis: elemental microanalyzer CHN CORDER MT-6 manufactured by Yanaco Co., Ltd., Cl analysis: automatic titrator COM-980win manufactured by Hiranuma Sangyo Corp.

Reference Example

Compound A was synthesized according to the method described in Patent Literature 1.

Example 1

Preparation of Acid-Adduct Salts of Compound a and Crystallinity Evaluation on Compound a and Acid-Adduct Salts (1) Preparation of Monohydrochloride Dihydrate of Compound A 1 mol/L hydrochloric acid (74 μL) was added to 7-[(1R,5S)-1-amino-5-fluoro-3-azabicyclo[3.3.0]octan-3-yl]-6-fluoro-1-[(1R,2S)-2-fluorocyclopropan-1-yl]-1,4-dihydro-8-methyl-4-oxoquinoline-3-carboxylic acid (compound A) (31.3 mg, 0.074 mmol), and the mixture was dried under reduced pressure at room temperature. To the residue, 10% aqueous 2-propanol (100 μL) was added, and the residue was dissolved by heating at 60° C. and then left at room temperature for 1 day. The precipitated crystals were collected by filtration and dried in air for 1 day to obtain 19.9 mg (yield: 54%).

Elemental analysis: $C_{21}H_{22}F_3N_3O_3 \cdot HCl \cdot 2H_2O$

Theoretical value: C, 51.07; H, 5.51; N, 8.51; F, 11.54; Cl, 7.18

Measured value: C, 50.93; H, 5.40; N, 8.49; F, 11.30; Cl, 7.47.

Characteristic diffraction peaks in powder X-ray diffraction: 2θ=5.3, 7.9, 10.6, 13.3, 21.1, 23.0, 25.1, and 27.6(°)

(2) Preparation of monohydrochloride monohydrate of compound A

5% aqueous 2-propanol (30 mL) was added to compound A (1001.6 mg, 0.746 mmol), and the compound was dissolved by heating at 60° C. The solution was stirred at room temperature for 1 day and then stirred at 10° C. for 6 hours. The precipitated crystals were collected by filtration and dried in air for 1 day to obtain 839.3 mg (yield: 87%).

Elemental analysis: C21H22F3N3O3.HCl.1H2O

Theoretical value: C, 53.00; H, 5.30; N, 8.83; F, 11.98; Cl, 7.45.

Measured value: C, 53.25; H, 5.43; N, 8.51; F, 11.58; Cl, 7.18;

Characteristic diffraction peaks in powder X-ray diffraction: 2θ=11.3, 14.0, 20.1, 21.4, 22.8, 24.0, 26.0, and 26.6(°)

(3) Preparation of Hydrobromide (Monohydrobromide Dihydrate) of Compound A

Hydrobromic acid (36 μL; 1 mol/L) was added to compound A (15.2 mg, 0.036 mmol), and the mixture was dried. To the residue, 10% aqueous 2-propanol (100 μL) was added, and the residue was dissolved by heating at 60° C. The solution was left at room temperature for 1 day. Then, the precipitated crystals were collected by filtration and dried in air for 1 day.

Characteristic diffraction peaks in powder X-ray diffraction: 2θ=13.8, 14.3, 20.2, 22.6, 25.2, 26.5, 30.0, and 31.0(°)

(4) Preparation of Hydrobromide (Monohydrobromide Monohydrate) of Compound A

Hydrobromic acid (48 μL; 1 mol/L) was added to compound A (20.2 mg, 0.048 mmol), and the mixture was dried. To the residue, 10% aqueous 2-propanol (750 μL) was added, and the residue was dissolved by heating at 60° C. The solution was left at room temperature for 5 days. Then, the precipitated crystals were collected by filtration and dried in air for 1 day.

Characteristic diffraction peaks in powder X-ray diffraction: 2θ=16.1, 19.5, 23.7, 24.6, 24.8, 25.5, 30.9, and 35.2(°)

(5) Preparation of Sulfate of Compound A

Sulfuric acid (49 μL; 1 mol/L) was added to compound A (20.4 mg, 0.049 mmol), and the mixture was dried. To the residue, 10% aqueous 2-propanol (150 μL) was added, and the residue was dissolved by heating at 60° C. The solution was left at room temperature for 7 days. Then, the precipitated crystals were collected by filtration and dried in air for 1 day.

Characteristic diffraction peaks in powder X-ray diffraction: 2θ=12.3, 14.6, 18.6, 21.7, 22.9, 24.6, 26.1, and 27.7(°)

(6) Preparation of p-Toluenesulfonate of Compound A

A solution of p-toluenesulfonic acid in ethanol (49 μL; 1 mol/L) was added to compound A (20.5 mg, 0.049 mmol). Then, 2-propanol (150 μL) was added thereto, and the mixture was dissolved by heating at 60° C. The solution was left at room temperature for 1 day. Then, the precipitated crystals were collected by filtration and dried in air for 1 day.

Characteristic diffraction peaks in powder X-ray diffraction: 2θ=8.0, 8.6, 18.5, 21.5, 22.2, 25.2, 25.8, and 27.4(°)

(7) Crystals 1 of Compound A in Free Form

Crystals of the free form were obtained according to the method of Patent Literature 1.

Characteristic diffraction peaks in powder X-ray diffraction: 2θ=7.6, 11.0, 14.9, 16.9, 18.3, 26.1, 26.4, and 26.9(°)

(8) Crystals 2 of Compound A in Free Form

20% aqueous 2-propanol (1000 μL) was added to compound A (15.3 mg, 0.036 mmol), and the compound was dissolved by heating at 60° C. The solution was left at room temperature for 1 day. Then, the precipitated crystals were collected by filtration and dried in air for 1 day.

Characteristic diffraction peaks in powder X-ray diffraction: 2θ=9.4, 14.1, 14.9, 18.9, 20.7, 23.1, 25.0, and 25.8(°)

Both the free forms, both the hydrochlorides, both the hydrobromides, the sulfate, and the p-toluenesulfonate of compound A each exhibited diffraction peaks in powder X-ray diffraction and were confirmed to be crystalline powders.

Example 2

Evaluation of Moisture Absorption and Desorption Properties

Of the various samples prepared in Example 1, the monohydrochloride dihydrate, monohydrochloride monohydrate, and sulfate were separately placed in quartz holders and examined for their moisture absorption and desorption behaviors using a microbalance under the following measurement conditions:

Measurement conditions for moisture absorption and desorption behavior (sample volume: approximately 10 mg, measurement range: 10-90% RH, measurement temperature: 25° C., variable: within 0.03%, varying length of time: 10 minutes, apparatus: atmospheric pressure-type automatic water vapor sorption instrument manufactured by VTI Corp.)

The results are shown in FIGS. 3, 6, and 13.

Both the hydrochlorides and the sulfate of compound A exhibited favorable moisture absorption and desorption behaviors with a change in weight of 2% or less at a relative humidity of 40% to 60%. Particularly, the moisture absorption and desorption patterns of the monohydrochloride dihydrate or the sulfate were well consistent. Particularly, the monohydrochloride dihydrate had no divergence between these moisture absorption and desorption patterns, indicating favorable behavior.

Example 3

Evaluation of Solubility

The monohydrochloride dihydrate prepared in Example 1 and the free form (anhydrous form) were used in the following evaluation of solubility: an appropriate amount of each sample was added to 2 mL each of the test solutions (water, the JP 1st fluid for the disintegration test (JP1), and the JP 2nd fluid for the disintegration test (JP2)), fasted state simulated intestinal fluid (FaSSIF), and fed state simulated intestinal fluid (FeSSIF), and incubated in a thermobath of 37° C. Each solution was shaken in a vortex mixer for 30 seconds every 5 minutes (for a total of 30 minutes). Then, the supernatant was filtered through a membrane filter (pore size: 0.45 μm). After appropriate dilution with an eluent, the diluted solution was subjected to HPLC analysis to calculate concentration.

Measurement conditions for HPLC;

Column: Waters Symmetry C18 3.5 um, 4.6×100 mm

Column temperature: 40° C.

Mobile phase: 50 mM KH2PO4-K2HPO4 (pH 7.0)/MeCN=8:2

Flow rate: 1 mL/min

Detection: UV 290 nm

The results are shown in Table 1.

TABLE 1

| | Concentration(μg/mL) | |
| --- | --- | --- |
| Test solution | Monohydrochloride dihydrate | Free form (anhydride) |
| Water | >2000 | 280 |
| JP 1st fluid for dissolution test | >2000 | >2000 |
| JP 2nd fluid for dissolution test | >2000 | 352 |
| Fasted state simulated intestinal fluid(FaSSIF) | >2000 | 319 |
| Fed state simulated intestinal fluid(FeSSIF) | >2000 | >2000 |

Example 4

Evaluation of Chemical Stability

Approximately 2 mg each of various samples prepared in Example 1 was weighed into an aluminum pan for thermal analysis and stored under dry-heat (60° C., 0% RH) or wet-heat (40° C., 75% RH) conditions. One and two weeks later, each sample was collected, and the change in weight was determined. Then, the whole amount was dissolved in 20 mL of an eluent and subjected to HPLC analysis.

The results are shown in Table 2.

TABLE 2

| Storage conditions | Increase in related substances (%) | |
|---|---|---|
| | Monohydrochloride dihydrate | Free form (anhydride) |
| 60° C./0% RH, 2 weeks | 0.02 | 0.01 |
| 40° C./75% RH, 2 weeks | 0.01 | 0.01 |

The invention claimed is:

1. 7-[(1R,5S)-1-amino-5-fluoro-3-azabicyclo[3.3.0]octan-3-yl]-6-fluoro-1-[(1R,2S)-2-fluorocyclopropane]-1,4-dihydro-8-methyl-4-oxoquinoline-3-carboxylic acid monohydrochloride.

2. 7-[(1R,5S)-1-amino-5-fluoro-3-azabicyclo[3.3.0]octan-3-yl]-6-fluoro-1-[(1R,2S)-2-fluorocyclopropane]-1,4-dihydro-8-methyl-4-oxoquinoline-3-carboxylic acid monohydrochloride dihydrate.

3. The compound according to claim 2, wherein the compound is a crystal.

4. The compound according to claim 3, wherein the compound is a crystal having characteristic peaks at diffraction angles (2θ) of 5.3, 7.9, 10.6, 13.3, 21.1, 23.0, 25.1, and 27.6(°) in powder X-ray diffraction.

5. A pharmaceutical composition comprising the compound according to claim 1 and one or more pharmaceutical additives.

6. A method of treating infections comprising administering the compound according to claim 1 to a human, animal or fish 4.

7. A pharmaceutical composition comprising the compound according to claim 2 and one or more pharmaceutical additives.

8. A pharmaceutical composition comprising the compound according to claim 3 and one or more pharmaceutical additives.

9. A pharmaceutical composition comprising the compound according to claim 4 and one or more pharmaceutical additives.

10. A method of treating infections comprising administering the compound according to claim 2 to a human, animal or fish.

11. A method of treating infections comprising administering the compound according to claim 3 to a human, animal or fish.

12. A method of treating infections comprising administering the compound according to claim 4 to a human, animal or fish.

* * * * *

UNITED STATES PATENT AND TRADEMARK OFFICE
CERTIFICATE OF CORRECTION

| | | |
|---|---|---|
| PATENT NO. | : 8,674,107 B2 | Page 1 of 1 |
| APPLICATION NO. | : 13/814534 | |
| DATED | : March 18, 2014 | |
| INVENTOR(S) | : Makoto Ono | |

It is certified that error appears in the above-identified patent and that said Letters Patent is hereby corrected as shown below:

In the Claims:

In claim 6, in column 12, at line 12, delete "fish 4." And insert -- fish. --

Signed and Sealed this
Seventeenth Day of June, 2014

Michelle K. Lee
*Deputy Director of the United States Patent and Trademark Office*